(12) United States Patent
Vinci

(10) Patent No.: US 12,277,816 B2
(45) Date of Patent: Apr. 15, 2025

(54) DEVICE FOR DECONTAMINATION OF OBJECTS AND FOR CONTROL DECONTAMINATION

(71) Applicants: Régine Vinci, Perpignan (FR); Axel Llobet, Saint Esteve (FR); Daniel Carbognani, Millas (FR)

(72) Inventor: Régine Vinci, Perpignan (FR)

(73) Assignees: RÉgine Vinci, Perpignan (FR); Axel Llobet, Saint Esteve (FR); Daniel Carbognani, Millas (FR)

( * ) Notice: Subject to any disclaimer, the term of this patent is extended or adjusted under 35 U.S.C. 154(b) by 88 days.

(21) Appl. No.: 18/058,018

(22) Filed: Nov. 22, 2022

(65) Prior Publication Data

US 2023/0177898 A1   Jun. 8, 2023

(30) Foreign Application Priority Data

Dec. 8, 2021 (FR) ..................... 2113147

(51) Int. Cl.
*G07C 9/00* (2020.01)
*A61L 2/00* (2006.01)

(52) U.S. Cl.
CPC ........ *G07C 9/00182* (2013.01); *A61L 2/0088* (2013.01); *G07C 9/00896* (2013.01); *A61L 2202/14* (2013.01); *G07C 2009/0019* (2013.01)

(58) Field of Classification Search
CPC ............ G07C 9/00182; G07C 9/00896; G07C 2009/0019; G07C 2209/08; G07C 9/20; A61L 2/0088; A61L 2202/14; A61L 2/10; A61L 2/24; G16H 40/63; G16H 40/20

USPC ....................... 340/5.7, 5.28, 10.1
See application file for complete search history.

(56) References Cited

U.S. PATENT DOCUMENTS

| | | | | |
|---|---|---|---|---|
| 6,975,231 B2* | 12/2005 | Lane | ............... | G08B 21/245 340/603 |
| 7,898,407 B2* | 3/2011 | Hufton | ............... | G08B 21/245 340/286.07 |
| 8,482,406 B2* | 7/2013 | Snodgrass | ............ | G08B 21/245 340/539.12 |
| 8,633,816 B2* | 1/2014 | Snodgrass | ............ | G16H 40/20 340/286.07 |
| 9,135,805 B2* | 9/2015 | Freedman | ............ | G08B 21/245 |
| 9,433,474 B2* | 9/2016 | Swinney | ............... | G16H 40/20 |
| 9,524,632 B2* | 12/2016 | Moore | ............... | G08B 21/245 |
| 9,965,943 B2* | 5/2018 | Borke | ............... | G16H 40/20 |

(Continued)

*Primary Examiner* — Nam V Nguyen
(74) *Attorney, Agent, or Firm* — INNOVATION CAPITAL LAW GROUP, LLP; Vic Lin

(57) ABSTRACT

The invention relates to a decontamination control system for an establishment comprising at least one sensitive room (L), comprising: a decontaminator (D1); —at least one badge (I) with an NFC tag, and/or at least one object (T) bearing an NFC tag; a first clock (H1) of the decontaminator (D1); a sabot (S) at the entrance to said room (L), comprising an NFC reader and a second clock (H2) synchronous with the first. According to the invention, the system triggers the decontaminator (D1) when said badge (I) is appended thereunto and/or said object (T) is introduced therein, and writes the corresponding timestamp on said NFC tag; then authorizes entry (E) into said room (L) if a first period (A) between the timestamp and the reading on the sabot (S) is less than a second threshold period (B); in the opposite case, the system prohibits said entry (E).

4 Claims, 2 Drawing Sheets

(56) References Cited

U.S. PATENT DOCUMENTS

| | | | |
|---|---|---|---|
| 10,529,219 B2* | 1/2020 | Herdt | G08B 25/10 |
| 11,426,477 B2* | 8/2022 | Dobrovolsky | A61L 2/24 |
| 2010/0090837 A1* | 4/2010 | Jung | A61L 2/10 |
| | | | 340/573.1 |
| 2015/0258233 A1* | 9/2015 | Brown | A61L 2/24 |
| | | | 422/292 |
| 2018/0330598 A1* | 11/2018 | Smith | G16H 40/20 |

* cited by examiner

DEVICE FOR DECONTAMINATION OF OBJECTS AND FOR CONTROL DECONTAMINATION

BACKGROUND OF THE INVENTION

This description stems from the following finding.

Various objects carried by hospital staff, such as mobile phones, watches, key rings, jewelry, are contaminated and follow these people into sensitive rooms, such as operating rooms.

Many publications confirm that these objects are contaminated by a wide variety of pathogenic germs and viruses, resulting in the emergence of nosocomial diseases.

To combat this phenomenon, the remedy would be to prohibit the introduction of these objects into sensitive rooms.

It seems, however, that some of these objects, such as the telephone, are very useful, if not essential, in certain care facilities, such as surgery.

In order to fight against these contaminations, from objects to patients, the most obvious way is to decontaminate these objects before they enter sensitive rooms.

However, this presupposes discipline on the part of the staff, unfortunately, not often respected.

Thus, an objective of the present invention is to propose a decontamination control system and method making it possible to ensure that hospital personnel enter sensitive places such as operating rooms, having decontaminated their objects, and preferably their hands.

SUMMARY OF THE INVENTION

In order to meet this objective, the invention proposes a decontamination control system for an establishment comprising at least one sensitive room, the decontamination control system comprising:
  a decontaminator;
  at least one badge with an NFC tag included or pasted thereto, and/or at least one object carrying an NFC tag;
  a first clock providing the day and time of decontamination by means of the decontaminator;
  a sabot at the entrance to said sensitive room, comprising an NFC tag reader and being equipped with a second clock synchronous with the first clock of the decontaminator,
  characterized in that the system is configured to trigger decontamination by the decontaminator when said badge is appended thereunto or introduced therein and/or said object is introduced therein, and to write the day and the time of decontamination on said NFC tag by a specialized circuit;
  and in that the system is configured to authorize entry into said sensitive room if a first period corresponding to the time elapsed between the time and the day of decontamination, to the time and the day of presentation of said badge and/or of said object to the sabot, is less than a second predetermined period to consider persistence of the decontamination; in the opposite case, the system is configured to prohibit said entry into said sensitive room.

By "decontaminator" is meant an apparatus making it possible to decontaminate, sterilize, substantially eliminate germs and other sources of nosocomial diseases.

Advantageously, the invention makes it possible to condition access to the sensitive room on the decontamination of objects and/or the washing of hands, which greatly limits the risk of nosocomial diseases.

The present invention is based on an innovative device, allowing the entry of these objects only if they are decontaminated and/or the hands are washed, and in a strict and unavoidable manner.

According to an embodiment, the decontaminator forms a hydroalcoholic product dispenser, comprising a container of a hydroalcoholic product, the decontamination being the washing of the hands by means of the hydroalcoholic product.

This enables to ensure that the hands of healthcare personnel are decontaminated.

According to an embodiment, the decontaminator comprises a decontamination volume that can be closed by a cover. This enables to ensure the decontamination of objects transported by health personnel to sensitive rooms. The objects to be decontaminated are introduced into the enclosure to carry out a thorough decontamination.

According to an embodiment, the decontamination control system further comprises a container of a hydroalcoholic product associated with the decontaminator, the decontamination control system being configured to servocontrol the opening of the cover of the decontaminator and/or its operation at an automatic and simultaneous dispensing of the hydroalcoholic product, the decontamination comprising exposure of the objects to a means for decontamination in said decontamination volume, and washing of the hands by means of the hydroalcoholic product.

This enables to condition access to the sensitive room both on the decontamination of objects and on the use of the hydroalcoholic product.

According to an embodiment, the clocks are synchronized to a radio signal, preferably that of the DCF transmitter 77; or on legal time.

This enables to ensure perfect synchronization of the clocks.

According to an embodiment, the sabot comprises a keyboard enabling to set, for the corresponding sensitive room, the time for the supposed persistence of decontamination of the objects placed in the decontaminator.

This enables to configure or reconfigure the second period.

According to an embodiment, said object comprises a mobile phone, a watch, a key ring, and/or jewelry.

This enables to limit the operations of movement and storage of these objects, and to limit the risk of loss of these objects. The telephone may be important to decontaminate in order to be able to use it in the sensitive room.

According to an embodiment, said decontaminator comprises an activation means for activating the dispensing of hydroalcoholic product by detection of hand in a distribution path of the hydroalcoholic product.

This enables to ensure that the hands have actually been in contact with the hydroalcoholic product. In addition, this makes it possible to trigger contactless dispensing.

The invention further concerns an establishment comprising:
  at least one sensitive room, and
  a decontamination control system according to the invention.

Another subject-matter of the invention relates to a decontamination control method for an establishment comprising at least one sensitive room, using the following devices:
  a decontaminator;
  at least one badge with an NFC tag included or pasted thereto, and/or at least one object carrying an NFC tag;

a first clock providing the day and time of decontamination by means of the decontaminator;

a sabot at the entrance to said sensitive room, comprising an NFC tag reader and being equipped with a second clock synchronous with the first clock of the decontaminator, characterized in that it comprises:

a decontamination step for triggering decontamination by the decontaminator when said badge is appended thereunto or introduced therein and/or said object is introduced therein, and writing the day and time of the decontamination on said NFC tag by a specialized circuit;

an authorization step for authorizing entry into said sensitive room if a first period corresponding to the time spent between the time and day of decontamination, to the time and day of presentation of said badge and/or of said object to the sabot is less than a second predetermined period to consider persistence of the decontamination;

in the opposite case, a prohibition step for prohibiting said entry into said sensitive room.

BRIEF DESCRIPTION OF THE DRAWINGS

The invention will be further detailed on the basis of the attached figures illustrating embodiments of the invention, namely.

DETAILED DESCRIPTION OF THE INVENTION

Figure 1:
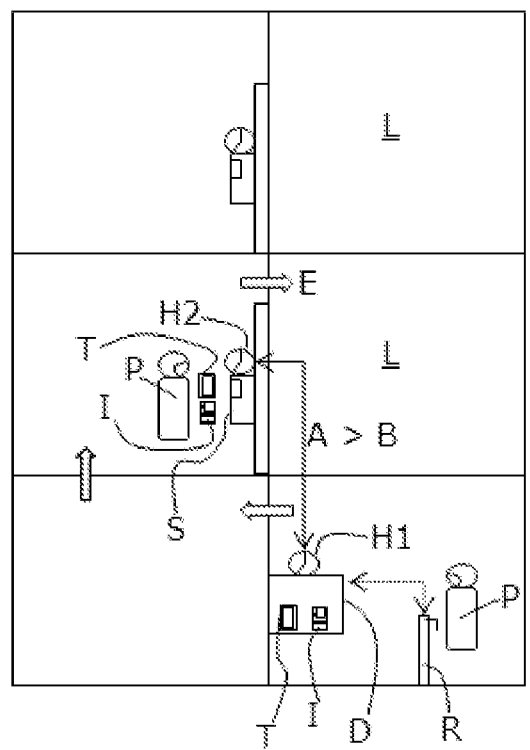
FIG. 1 schematically illustrates a healthcare establishment according to a first preferred embodiment of the invention with telephone decontamination and hand washing with hydroalcoholic gel.
Figure 2:
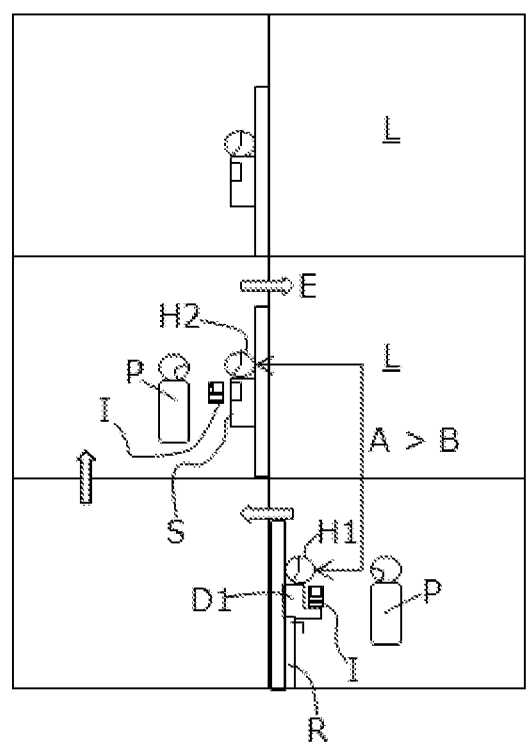
FIG. 2 schematically illustrates a healthcare establishment according to a second embodiment with hand washing with hydroalcoholic gel.

The present invention is based on an innovative system, authorizing the entry (E) of objects of health personnel P only if they are decontaminated, and in a strict and unavoidable manner.

Thus, the first embodiment of the invention proposes a system allowing the verification of the decontamination of hands and other objects, with a view to controlling access to sensitive rooms in healthcare establishments. This system combines traceability of decontaminated objects T, in the form of information conveyed by the passage of time counted on a universal clock, and controls access to the sensitive room L.

It is based on four physical parts:

a decontaminator D;

a device for tracking decontaminated T objects using NFC tags carried by objects T;

a clock H1 providing the day and time in the decontaminator D, this clock being synchronous with all the clocks of the establishment. This last result being obtained, for example, by synchronizing on a radio signal like the DCF 77 transmitter;

a sabot S at the entrance to the sensitive room L, comprising an NFC tag reader and being equipped with a clock synchronous with the clock H1 of the decontaminator D.

Decontaminator D is in particular a UVC (LED) decontaminator enclosure equipped with a cover, and an electrically controlled closing/opening lock.

Decontaminator D includes an electronic device for writing the time on the NFC tag.

The sabot S comprises a means for generating a signal authorizing the urgent entry, for example a loudspeaker.

By way of non-limiting example of embodiment, the operation, described below, makes it possible to better understand the invention.

The object to be decontaminated chosen in this example: a mobile phone T, on which an NFC tag has been pasted. The telephone T thus equipped is introduced into the decontaminator D.

Simultaneously, the decontaminator D and the writing of the day and time on the tag are triggered by a specialized circuit.

After a few seconds, the decontamination having been completed, the telephone T is removed by the person who plans to use it in the sensitive room L. This same person, in order to enter the sensitive room L, presents the telephone T to the reader of the sabot S. The latter reads the time and day written on the tag of the telephone and compares them with the time and day of its clock H2, synchronous with the clock H1 of the decontaminator D.

It deduces the time spent between the time and the day of entry of the telephone T into the decontaminator D, and the time and day of presentation of the same telephone T to the sabot S by the person wishing to enter the sensitive room L with this telephone T.

This period A, thus determined, is compared, by the sabot S, to the period B, decided for the room L, during which the telephone T is considered sterile.

If A is less than B, an authorization to enter is activated by sabot S.

in the opposite case, the sabot S displays a no-entry signal.

In a second non-limiting example of this first embodiment, the NFC tag is included in and/or pasted to the badge card I carried by the healthcare personnel P.

To be able to enter a sensitive room L, the bearer of the badge I introduces it into the decontaminator D, as already described, and takes the opportunity to add all the possibly contaminated objects T, which he will carry in the room L. For efficiency, before extracting the badge I and the objects T from the decontaminator D, he will disinfect his hands.

In this configuration, and also all the others, the opening of the cover of the decontaminator D and/or its operation can be servocontrolled to the automatic and simultaneous distribution of a hydroalcoholic hand disinfection product by a container R associated with the decontaminator D, in particular directly connected to the decontaminator D.

In a third non-limiting example of this embodiment, the time and day of the clock H1 of the decontaminator D and that (H2) of the sabot S, at the entrance to the room L, are initialized from legal time, are therefore synchronous. Their operating time, thanks to a long-lasting battery, exceeds 10 years, and will not drift by more than 1 second for these 10 years, thanks to the technologies of current watches and quartz-driven clocks.

The reading sabot S, at the entrance to the sensitive room L also comprises a keyboard enabling to set for this room L, the period B of supposed persistence of decontamination of the objects T deposited in the decontaminator D.

The time during which the hands are deemed to be decontaminated is programmable for each sensitive room L, on the sabot S comprising the tag reader.

The sabot S includes a circuit delivering a signal authorizing or prohibiting entry into the room.

In conclusion, this device, object of the invention, is innovative by its principle using as identifier of decontaminated objects T, the time and day of decontamination, implies traceability, thanks to the choice of the identifier. In addition, it does not require any radio or wire link between the decontaminator D and the entrance to the room.

The system may include a computerized device for analyzing the frequency of system traffic.

Information is conveyed by the passage of time. It is universal by virtue of these choices, usable anywhere in the world, as designed, with a minimum of constraints, both technological and human, for a modest price.

The second embodiment of the invention is similar to the first, with emphasis on disinfection of hands, but decontamination of objects is not provided for in it.

Thus, the access control system is simplified (without the UVC decontaminator D). The decontaminator D1 used is a hydroalcoholic product dispenser.

The system works as follows:
placing the badge I (worn by each staff member P) on the gel dispenser D1 fitted with the time writing electronics;
presenting the hands under the jet of gel, triggered by a cell, the gel triggering signal then controlling the writing of the time on the badge I;
the badge I thus written is used for the control on the sabot S, as already described.

The two devices D, D1 can exist simultaneously, depending on the needs of the sensitive rooms L.

In the preferred variant, the decontaminator D1 can be triggered either manually or by detection of the hands under a distribution path of the hydroalcoholic product. It is for example an activation element coupled to a sensor, such as an infrared sensor.

The invention claimed is:

1. A decontamination control system for an establishment comprising at least one sensitive room, the decontamination control system comprising:
   a decontaminator forming a hydroalcoholic product dispenser, comprising a container of a hydroalcoholic product;
   at least one badge with a Near Field Communication (NFC) tag included or pasted thereto, and/or at least one object carrying an NFC tag;
   a first clock providing a first day and time of decontamination by means of the decontaminator;
   a sabot at an entrance to said sensitive room, comprising an NFC tag reader and being equipped with a second clock synchronous with the first clock of the decontaminator providing a second day and time,
   wherein the system is configured to trigger decontamination by the decontaminator when said badge is appended thereunto or introduced therein, and to write the first day and time of decontamination on said NFC tag by a specialized circuit;
   wherein the system is configured to authorize entry into said sensitive room if a first period corresponding to the time elapsed between the first time and day of decontamination, to the second time and day of presentation and appendance of said badge unto the sabot, is less than a second predetermined period to consider persistence of the decontamination; in the opposite case, the system is configured to prohibit said entry into said sensitive room,
   and wherein the decontaminator comprises an activation means for activating the dispensing of hydroalcoholic product by detection of hand in a distribution path of the hydroalcoholic product, such that a gel triggering signal is then controlling the writing of the time on the badge.

2. The decontamination control system according to claim 1, characterized in that the clocks are synchronized to a radio signal, preferably that of the long wave signal transmitter (DCF77); or on legal time.

3. An establishment comprising at least one sensitive room, and a decontamination control system comprising:
   a decontaminator forming a hydroalcoholic product dispenser, comprising a container of a hydroalcoholic product;
   at least one badge with a Near Field Communication (NFC) tag included or pasted thereto, and/or at least one object carrying an NFC tag;
   a first clock providing a first day and time of decontamination by means of the decontaminator;
   a sabot at an entrance to said sensitive room, comprising an NFC tag reader and being equipped with a second clock synchronous with the first clock of the decontaminator providing a second day and time,
   wherein the system is configured to trigger decontamination by the decontaminator when said badge is appended thereunto or introduced therein, and to write the first day and time of decontamination on said NFC tag by a specialized circuit;
   wherein system is configured to authorize entry into said sensitive room if a first period corresponding to the time elapsed between the first day and time of decontamination, to the second day and time of presentation and appendance of said badge unto the sabot, is less than a second predetermined period to consider persistence of the decontamination; in the opposite case, the system is configured to prohibit said entry into said sensitive room,
   and wherein the decontaminator comprises an activation means for activating the dispensing of hydroalcoholic product by detection of hand in a distribution path of the hydroalcoholic product, such that a gel triggering signal is then controlling the writing of the time on the badge.

4. A decontamination control method for an establishment comprising at least one sensitive room, using the following devices:
   a decontaminator forming a hydroalcoholic product dispenser, comprising a container of a hydroalcoholic product;
   at least one badge with a Near Field Communication (NFC) tag included or pasted thereto, and/or at least one object carrying an NFC tag;
   a first clock providing a first day and time of decontamination by means of the decontaminator;
   a sabot at an entrance to said sensitive room, comprising an NFC tag reader and being equipped with a second clock synchronous with the first clock of the decontaminator providing a second day and time,
   wherein it comprises:
   a decontamination step for triggering decontamination by the decontaminator when said badge is appended thereunto or introduced therein, and writing the first day and time of the decontamination on said NFC tag by a specialized circuit,
   wherein the decontamination step comprises activating the dispensing of hydroalcoholic product by detection of hand in a distribution path of the hydroalcoholic product, such that a gel triggering signal is then controlling the writing of the time on the badge;

an authorization step for authorizing entry into said sensitive room if a first period corresponding to the time spent between the first day and time of decontamination, to the second day and time of presentation and appendance of said badge unto the sabot is less than a second predetermined period to consider persistence of the decontamination;

in the opposite case, a prohibition step for prohibiting said entry into said sensitive room.

\* \* \* \* \*